United States Patent [19]
Mooi

[11] 4,118,430
[45] Oct. 3, 1978

[54] PROCESS FOR THE ISOMERIZATION OF HYDROCARBONS

[75] Inventor: John Mooi, Homewood, Ill.

[73] Assignee: Atlantic Richfield Company, Los Angeles, Calif.

[21] Appl. No.: 681,375

[22] Filed: Apr. 29, 1976

[51] Int. Cl.² ............................................. C07C 15/08
[52] U.S. Cl. ............................ 260/668 A; 260/683.65; 208/120
[58] Field of Search ................... 208/120; 260/668 A, 260/683.65

[56] References Cited

U.S. PATENT DOCUMENTS

| | | | |
|---|---|---|---|
| 3,140,249 | 7/1964 | Plank et al. | 208/120 |
| 3,856,872 | 12/1974 | Morrison | 260/668 A |

OTHER PUBLICATIONS

Chem. Ab. 83:100653x, Ger. Offen. 2,444,911 Schwartz 4/3/75.

*Primary Examiner*—Veronica O'Keefe
*Attorney, Agent, or Firm*—Coleman R. Reap

[57] ABSTRACT

An improved process for isomerizing hydrocarbons using a catalyst which is periodically regenerated to remove carbonaceous deposits, the catalyst being comprised of a mixture containing, as a major component, an isomerization catalyst free of carbon monoxide-oxidizing metals or metal compounds, and, as a minor component, an isomerization catalyst which contains small amounts of a metal or a compound of a metal selected from vanadium and the metals of Groups IB, VIB, VIIB and VIII of the Periodic Table. The process is particularly suitable for the isomerization of metaxylene to a mixture of orthoxylene and paraxylene.

9 Claims, No Drawings 4,118,430

PROCESS FOR THE ISOMERIZATION OF HYDROCARBONS

BACKGROUND

Field of the Invention

This invention relates to the isomerization of hydrocarbons and more particularly to the vapor phase isomerization of hydrocarbons by means of a metal-containing catalyst which is periodically regenerated to remove carbonaceous deposits.

The term "isomerization" is used herein to describe the conversion of a hydrocarbon into at least one different hydrocarbon product having the same number of carbon atoms. Isomerization is particularly useful for the conversion of straight chain paraffinic hydrocarbons such as n-butane into isobutane and for the conversion of aromatic hydrocarbons such as metaxylene into a mixture of orthoxylene and paraxylene.

Hydrocarbon isomerization is carried out commercially by contacting the hydrocarbon to be isomerized with a catalytic material at elevated temperatures and at pressures ranging from atmospheric to several hundred psi. The catalyst usually has a relatively long life since it is not, to any great extent, permanently affected by the isomerization reaction. However, when isomerization is carried out in the vapor phase there is a rapid buildup of carbonaceous deposits, such as coke, on the catalyst. These deposits must be frequently removed as they rapidly inactivate the catalyst. The catalyst is regenerated by burning off the carbonaceous deposit in the presence of free oxygen. During the catalyst regeneration carbon monoxide and carbon dioxide are produced as gaseous combustion products, the relative amounts of each depending upon the efficiency of the oxidation step.

Recent federal and local air pollution control legislation has made it necessary to eliminate or drastically reduce the amount of carbon monoxide being discharged into the atmosphere. One method of accomplishing this is by contacting the gaseous effluent from the catalyst regenerator with an oxidation promoter to convert the carbon monoxide to carbon dioxide, however the cost of this operation is too great for economically practical operation of all but very large plants in which the production of carbon monoxide is great enough to justify the additional expenditure for a carbon monoxide conversion unit.

The elimination of carbon monoxide as a gaseous by-product from hydrocarbon conversion processes using a regenerative catalyst can also be effected by using a catalyst which contains a promoter, usually a metal or metal compound, for the conversion of carbon monoxide to carbon dioxide. U.S. Pat. No. 2,647,860 describes a hydrocarbon cracking process using a synthetic silicaalumina catalyst which is capable of regeneration, and and which contains about 0.01 to 1% by weight of chromic oxide to promote the oxidation of carbon monoxide in the catalyst regenerator. This patent acknowledges the fact that the chromic acid adversely affects the cracking reaction. U.S. Pat. No. 3,140,249 describes the preparation and use of crystalline aluminosilicate compositions containing small amounts of metals such as vanadium and manganese in hydrocarbon cracking processes. U.S. Pat. No. 3,140,253 discloses the preparation and use of crystalline aluminosilicates in hydrocarbon conversion processes, including hydrocarbon isomerization. This patent states that metal promoters such as chromium, cobalt and platinum may be present in the catalyst in amounts of about 5 to 40% by weight. U.S. Pat. No. 3,173,854 describes a process for the hydrocracking of hydrocarbon oils using a crystalline aluminosilicate containing, as a hydrogenation component, 0.01 to 25% by weight of a metal selected from Groups VI and VIII of Periodic Table. U.S. Pat. No. 3,650,990 discloses the preparation of a crystalline aluminosilicate useful for the conversion of hydrocarbons containing a metal promoter selected from Groups IVB, VB, VIB, VIIB and VIII of the Periodic Chart. The metal is incorporated into the crystalline aluminosilicate prior to or during its formation and may vary from .001 to 5% by weight. U.S. Pat. No. 3,788,977 describes hydrocarbon cracking using a platinum-impregnated crystalline aluminosilicate catalyst. The platinum which is present in amounts of 0.5 ppm or more increases the yield of aromatic product. The use of catalyts which contain carbon monoxide oxidizing metals or metal compounds in isomerization processes significantly reduces the efficiency of the catalyst for the hydrocarbon isomerization reaction.

U.S. Pat. No. 3,364,136 describes hydrocarbon conversion using a catalyst comprised of a first component consisting of solid particles containing a crystalline aluminosilicate which is active for the conversion of the hydrocarbon, and a second component consisting of solid particles containing a crystalline aluminosilicate which is inert with respect to the hydrocarbon conversion reaction because its pores are too small to admit the hydrocarbon reactant, but which is effective to promote oxidation of carbon monoxide to carbon dioxide. The latter component contains from less than 0.01 up to 20% by weight of a metal, metal oxide or metal sulfide from Groups IB, IIB, VIB, VIIB or VIII of the Periodic Chart. The disadvantage of this catalyst is that its use reduces the capacity of the reactor since only a portion of the catalyst is useful for hydrocarbon conversion. Belgian Pat. 820,181 describes a process for cracking hydrocarbons with a cracking catalyst material which contains less than the 100 ppm of a metal chosen from Periods 5 and 6 of Group VIII of the Periodic Chart or rhenium. This patent teaches that the metal may be applied uniformly over all of the catalyst or it may be applied at a higher concentration on a portion of the catalyst and blended with unmodified catalyst provided that the total metal content of the final catalyst mixture does not exceed 100 ppm.

SUMMARY

A method has now been discovered for significantly reducing the emission of carbon monoxide into the atmosphere in a hydrocarbon isomerization process using a catalyst which is periodically regenerated wth oxygen to remove carbonaceous deposits without significantly reducing the productive capacity of the isomerization reactor.

Accordingly, it is an object of this invention to present an improved process for isomerizing hydrocarbons, particularly aromatic hydrocarbons. It is another object of the invention to present an improved process for isomerizing hydrocarbons in the absence of added free molecular hydrogen. It is another object of this invention to present an improved process for isomerizing hydrocarbons, particularly aromatic hydrocarbons such as metaxylene, in a two-step reaction-catalyst regeneration process. It is another object of the invention to significantly reduce the amount of carbon monoxide produced during the regeneration of a catalyst used for the isomerization of hydrocarbons. It is another object of the invention to significantly reduce the emission of carbon monoxide into the atmosphere in a hydrocarbon isomerization process using a catalyst which is periodically regenerated to remove carbonaceous deposits without significantly reducing the productive capacity of the isomerization reactor. It is another object of the invention to present an improved hydrocarbon isomerization catalyst. These and other objects of the invention will become apparent from the following description and examples.

In accordance with the invention the isomerization-regeneration process is carried out using a mixture of solid particles comprised of (1) a major amount of first solid particles which are effective to promote the hydrocarbon isomerization reaction and which are substantially free of carbon monoxide oxidation metals or metal compounds and (2) a minor amount of second solid particles which are effective to promote the hydrocarbon isomerization and which contain a minor amount, preferably about 0.05 ppm to 10% and more preferably 1 ppm to 1% by weight of said second solid particles of at least one metal or a composition of a metal selected from Groups IB, VIB, VIIB and VIII of the Periodic Table and vanadium to promote the oxidation of carbon monoxide to carbon dioxide during the regeneration step. The preferred metal or metal compositions are those of the platinum series, particularly palladium and platinum. The preferred amounts of the first and second solid particles are about 80 to 99% and 1 to 20% by weight respectively. This catalyst system is especially effective for the isomerization of metaxylene to orthoxylene and paraxylene.

DESCRIPTION OF THE INVENTION

The improvement of this invention can be used to advantage in either fixed or circulating catalyst bed operations. It is usually preferable, however, to isomerize hydrocarbons by circulating catalyst bed techniques since the necessity for frequent catalyst regeneration to remove carbonaceous deposits on the catalyst particles renders the fixed bed method less practical. Of the circulating bed methods it is often preferable to use moving bed techniques rather than fluidized bed procedures.

The catalyst system used in the isomerization of hydrocarbons in accordance with the teachings of the invention is comprised of a mixture of two types of solid particles. The first solid particles are effective as a hydrocarbon isomerization catalyst and are substantially free of added metal or metal compound additives which are catalytically active for the oxidative conversion of carbon monoxide to carbon dioxide. Metals or metal compounds to be avoided in preparing the first component of the catalyst are the metals or metal compounds of vanadium and Groups IB, VIB, VIIB and VIII of the Periodic Table of the Elements. It has been determined that when a major portion of the solid particles used in hydrocarbon isomerization contains one or more of these metals or a compound of one or more of these metals the yield of desired products is often significantly reduced. It is particularly desirable to avoid incorporating the metals or compounds of metals of the platinum series of Group VIII, i.e., platinum, palladium, ruthenium, osmium, rhodium and iridium into the first solid particles used in the invention.

The second solid particles comprise at least one base material which is effective as a hydrocarbon isomerization catalyst and at least one metal or metal compound effective to promote the oxidation of carbon monoxide to carbon dioxide. The base material may have the same composition as the first solid particles or it may be a different hydrocarbon isomerization catalyst. The metals which have been found to be suitable for incorporation into the second solid particles in the practice of the invention are those which belong to Groups IB, VIB, VIIB and VIII of the Periodic Table and vanadium. Compounds of these metals can also be used in the second solid particles. Although any of the metals or metal compounds in these groups can be effectively used, it has been determined that metals or compounds of metals of the platinum series of Group VIII are preferred for use in the invention. The metals of the platinum series include platinum, palladium, rhodium, iridium, ruthenium and osmium. Platinum and palladium metals and their compounds are especially active for the promotion of the oxidation of carbon monoxide to carbon dioxide. These metals and their compounds, when incorporated into a minor amount of the total catalyst inventory used in the reactor provide improved overall catalyst performance, e.g., increased oxidation of carbon monoxide while having substantially no adverse effect on the hydrocarbon isomerization reaction.

The hydrocarbon isomerization catalyst used in the first and second solid particles may be of any of the natural or synthetic materials which are effective to catalytically promote the isomerization of hydrocarbons. Suitable materials include acid-treated natural clays such as montmorillonite, kaolin and bentonite clays, natural or synthetic porous amorphous materials such as amorphous, i.e., noncrystalline, silica-alumina, silica-magnesia and silica-zirconia composites, and the more recently developed crystalline aluminosilicates, often referred to as zeolites or molecular sieves. Porous amorphous silicaalumina, silica-magnesia and silica-zirconia composites, are preferred over the other mentioned catalysts since they are much more selective for the isomerization reaction. It is preferred that the pores in the amorphous silica composites have a diameter of at least about 10A. The method of preparation of these catalysts is well known and forms no part of this invention. The preparation of amorphous silica-alumina, etc. catalyst materials is described in the above-mentioned patents and the disclosures of these patents are incorporated herein by reference.

The metal may be incorporated into the base material as the metal or as a compound of the metal. Methods of incorporating metals or metal compounds into catalytic materials of the type used herein by impregnation or otherwise are well known and, in general, any of the known methods can be used in the preparation of the second solid particles used in the catalyst system of the invention. It is preferred, however, to use a method of metal incorporation which will provide for the uniform distribution of the metal in the second solid particles in a form which is not easily removable. The metal can be incorporated either during or after the formation of the second solid particles. A commonly used method of incorporating the metal into the second solid particles is to contact the particles with a solution, e.g., an aqueous solution, of the metal or a compound of the metal, followed by drying the particles to remove the solvent. Another useful method of incorporating the metal or metals into the second solid particles is ion exchange.

As stated above these or other known methods of incorporating metals or metal compounds into the second solid particles can be employed.

When the metal or metals are incorporated into the second solid particles as a compound the compound may be inorganic or organic. Representative classes of inorganic compounds include the oxides, sulfates, sulfides, oxychlorides, halides, nitrates, phosphates and other inorganic salts, preferably water-soluble salts, of the above metals. Typical inorganic compounds for incorporation into the second solid particles include copper nitrate, copper chloride, silver nitrate, chromic acid, chromium nitrate, ammonium molybdate, ammonium tungstate, manganous nitrate, ammonium perrhenate, perrhenic acid, ferric chloride, ferric nitrate, ferrous ammonium sulfate, cobalt chloride, cobalt nitrate, nickel nitrate, nickel chloride, ruthenium nitrate, ruthenium chloride, rhodium trichloride, ammonium palladium hexachloride, palladium chloride, diamminedichloropalladium, diamminedinitropalladium, tetraamminepalladium chloride, tetraamminepalladium hydroxide, palladium nitrate, palladium acetate, osmium tetroxide, ammonium platinum hexachloride, chloroplatinic acid, diamminodichloroplatinum, diamminedinitroplatinum, tetraammineplatinous hydroxide, tetraammineplatinous hydroxide, etc. As mentioned above, platinum series compounds, such as chloroplatinic acid, palladium chloride, osmium tetroxide, etc. are preferred because of their greater catalytic activity.

Representative classes of organic metal-containing compounds which can be used to incorporate the metal into the second solid particles include metal ketones, metal alcoholates, metal salts of organic acids, etc.

Typical organic compounds include bis(ethylacetoacetato) copper (II), copper acetylacetonate, silver palmitate, pentachloromolybdenum, hexacarbonylmolybdenum, tetrachloromolybdenum, hexacarbonylmolybdenum, tetrachloroxytungsten (VI), hexachlorotungsten (VI), $\pi$-cyclopentadienyltricarbonylmanganese (I), bis($\pi$-cyclopentadienyl)tricarbonylrhenium (II), trichloro(tetrahydrofuran)iron (III), tricarbonyl(cyclooctatetraene)iron, tetracarbonyltriphenylphosphinoiron, nitrosyltricarbonylcobalt (I), $\pi$-cyclopentadienyldicarbonylcobalt (I), ruthenocene, tricarbonyltris(triphenylphosphino) ruthenium, palladium acetylacetonate, tetrakis(triphenylphosphino)palladium, dichloro(ethylene) palladium (II) dimer, $\pi$-cyclopentadinyldicarbonylosmium(I)dimer, platinum acetylacetonate, dichlorodicarbonylplatinum (II), trimethylplatinum chloride, dichlorotetracarbonyldirhodium (I), chlorocarbonylbis(triphenylphosphino) rhodium (I), triiodotricarbonyliridium (III), trichlorobis(trichlorophosphino) iridium (III), etc. As above the platinum series organic series are preferred.

The amount of metal or metal compound incorporated into the second solid particles will depend upon the particular metal being used. For example, very small amounts of highly active metals such as platinum or palladium have been found to be effective whereas it is necessary to use larger amounts of less active metals to achieve the desired results. In general, it is desirable to incorporate into the second solid particles about 0.05 ppm to 10% and preferably about 0.5 ppm to 1% of the metal, or sufficient amounts of one or more metal compounds to provide this amount of metal, based on the total weight of the second solid particles. When a metal of the platinum series is used it is preferred that the amount of metal be in the range of about 0.05 to 1000 ppm and more preferably about 0.5 to 500 ppm calculated as elemental metal based on the total weight of second solid particles.

It may be desirable to separate the second solid particles from the first solid particles, for example, when it is desired to use the first solid particles alone for hydrocarbon conversion or where it is desired to recover the second solid particles for other uses or for metal recovery. This can be conveniently accomplished by preparing the second solid particles in a manner such that they have a different size than the first solid particles. The separation of the first and second solid particles can then be easily effected by screening.

The catalyst of the invention can be beneficially used for the isomerization of paraffinic or aromatic hydrocarbons. It is well adaptable to the isomerization of paraffinic hydrocarbons containing from 3 to 20 carbon atoms and aromatic hydrocarbons containing one or two rings and up to 18 carbon atoms. The process of the invention is particularly useful for the isomerization of methyl benzenes containing from 8 to about 10 carbon atoms per molecule and is especially useful for the isomerization of metaxylene to a mixture of orthoxylene and paraxylene.

In accordance with a preferred embodiment a hydrocarbon feedstock, such as metaxylene, which is in the vapor phase is isomerized in a moving catalyst bed reactor in which the catalyst is a mixture containing about 80 to 99% by weight of first solid particles which is a porous amorphous silica-alumina composition and about 1 to 20% of second solid particles which is an amorphous silica-alumina composition and which have incorporated therein about 0.05 ppm to 1000 ppm of at least one metal selected from the platinum series of Group VIII of the Periodic Table. The first and second solid particles preferably have a size, e.g., diameter of about 1/32 to 1 and more preferably about ⅛ to ¼ inch in size. The isomerization reaction zone is preferably operated at a temperature of about 700° to 1200° F. and more preferably about 800° to 1000° F. and preferably at approximately atmospheric pressures such as about 0 to 30 psig. The catalyst holding time, i.e., the length of time that the catalyst remains in the reaction zone is preferably kept in the range of about 6 to 240 and more preferably about 12 to 120 minutes. Longer holding times are generally undesirable since they result in higher coke buildup on the catalyst and thereby reduce the catalyst activity. The weight hourly space velocity (WHSV), that is, the weight of hydrocarbon feed per hour per unit weight of catalyst is preferably in the range of about 0.1 to 10 and more preferably about 0.25 to 5.

After the catalyst particles leave the isomerization reaction zone they enter the catalyst regeneration zone where the carbonaceous substances which were deposited on the catalyst particle surfaces during the isomerization reaction are removed. This is accomplished by contacting the catalyst with an oxygen-containing gas stream, such as air, at temperatures preferably in the range of about 800° to 1500° F. and more preferably about 900° to 1200° F. The oxygen-containing gas stream may be heated prior to its introduction into the regenerator. The temperature and flow rate of the oxygen-containing gas stream is preferably such that the temperature in the regeneration zone is maintained in the preferred temperature range specified above.

The following examples illustrate specific embodiments of the invention. Unless otherwise indicated, parts and percentages are on a weight basis.

EXAMPLE I

A

Particulate hydrocarbon isomerization catalyst in the shape of spheres having a diameter of about 1/16-¼ inch and comprised of porous amorphous silica-alumina is charged into a flask equipped with means for evacuating the flask. The flask is evacuated and maintained under a vacuum of 28 inches Hg for 20 minutes. An aqueous solution of chloroplatinic acid is introduced into the flask and the flask is agitated sufficiently to effect a uniform distribution of the chloroplatinic acid on the catalyst particles. The concentration of chloroplatinic acid in the solution is sufficient to impregnate the catalyst with 100 ppm, based on the weight of catalyst, of platinum, calculated as elemental platinum. The catalyst is dried in a hot air stream with continuous agitation for three hours and then calcined in an air stream in a tube furnace at 1200° F. for 1 hour. The catalyst is now ready for use.

B

The hydrocarbon isomerization catalyst mixture is prepared by combining 5 parts by weight of the above-prepared platinum-containing amorphous silica-alumina catalyst and 95 parts of the particulate amorphous silica-alumina catalyst used in the preparation of the platinum-containing catalyst. The catalyst mixture is packed into a 0.3 liter cylindrical quartz reactor 50 mm in diameter and 16 cm long equipped with a sleeve heater and a feed and product analyzer which measures the amount of carbon monoxide in the feed and product streams. The reaction zone of the reactor is maintained at a temperature of 1000° F. during the reaction. A feed mixture comprised of, on a volume basis, 5% carbon monoxide, 2.8% oxygen, 1% carbon dioxide and the balance nitrogen is passed through the reactor at a feed rate of 13.5 standard ft$^3$/hr (SCFH). The reaction is permitted to run for 40 minutes at constant flow conditions. During the reaction 98.7% of the carbon monoxide in the feed mixture is oxidized to carbon dioxide.

Example I shows that when small portions, for example, 5% of the total inventory of a catalyst is impregnated with unusually high levels of platinum compound (100 ppm) a very high percentage (98.7%) of the carbon monoxide present in a feed mixture which is passed through the bed is converted to carbon dioxide (compared to the percent conversion with totally platinum-free catalyst) in spite of the fact that the catalyst substrate does not itself promote the reaction of carbon monoxide to carbon dioxide.

EXAMPLE II

The procedure of Example IB is repeated except that the catalyst used is 100% porous silica-alumina catalyst (containing no added platinum). During the reaction only about 7% of the carbon monoxide in the feed will be converted to carbon dioxide.

EXAMPLE III

A hydrocarbon feed stream comprised of 9.3% by weight paraxylene, 79.0% by weight metaxylene and 11.7% by weight orthoxylene is isomerized by contacting it with the catalyst mixtures described above in Examples I and II. The reactor used in this example consists of a ½ inch diameter pyrex fixed bed tube fitted with a sleeve heater. The test is carried out by contacting the feed stream with the catalyst at a flow rate of 0.2 cc per minute for ten minutes. The Run 1 catalyst is unmodified particulate porous amorphous silica-alumina catalyst and the Run 2 catalyst mixture consists of a 5 weight % of 100 ppm platinum-impregnated amorphous silica-alumina catalyst and 95 weight % unmodified particulate amorphous silica-alumina catalyst. The results of this experiment are tabulated in Table I.

TABLE I

| Run | 1 | 2 |
|---|---|---|
| Feed Analysis, wt.% | | |
| paraxylene | 9.3 | 9.3 |
| metaxylene | 79.0 | 79.0 |
| orthoxylene | 11.7 | 11.7 |
| Catalyst | unmodified PAS* | 95% PAS* 5% Pt impregnated PAS* |
| Product Analysis, wt.% | | |
| paraxylene | 13.2 | 13.2 |
| metaxylene | 68.5 | 68.3 |
| orthoxylene | 15.3 | 15.4 |
| other hydrocarbons and carbon | 3.0 | 3.1 |
| % Approach to Equilibrium | | |
| paraxylene | 29 | 29 |
| metaxylene | 39 | 40 |
| orthoxylene | 27 | 28 |

*PAS - particulate porous amorphous silica-alumina

"% Approach to Equilibrium" is a measure of the effectiveness of the isomerization reaction and employs as a reference the percentages of the three xylene isomers existing at equilibrium at the reference temperature. At the reaction temperature, 900° F., the percentages of paraxylene, orthoxylene and metaxylene at equilibrium conditions are 23%, 25% and 52% by weight, respectively. The % approach to equilibrium for each of the three xylene components is determined by the following equation:

$$\% \text{ Approach} = \frac{\text{wt.\% component in product} - \text{wt.\% component in feed}}{\text{wt.\% component at equilibrium} - \text{wt.\% component in feed}} \times 100$$

This example illustrates the effectiveness of the catalyst of the invention as an isomerization catalyst. A compression of Runs 1 and 2 shows that the overall isomerization activity of the catalyst of the invention (Run 2) is not adversely affected by the presence of the platinum on 5% of the catalyst inventory.

EXAMPLE IV

When the feed stream used in Example III is isomerized at the conditions set forth in Example III using particulate porous amorphous silica-alumina containing 2 wt. % vanadium, the isomerization promotion activity of the particulate amorphous silica-alumina will be found to be substantially equivalent to porous amorphous silica-alumina which is free of added metals. When this catalyst is regenerated by combustion very little carbon monoxide will be formed as a gaseous product.

EXAMPLE V

When Example IV is repeated except that chromium is substituted for the vanadium, the isomerization promotion activity of the catalyst will be found to be substantially equivalent to the unmodified particulate porous amorphous silica-alumina. The resulting catalyst will also be found to possess excellent carbon monoxide oxidation activity.

EXAMPLE VI

Example IV is repeated except that manganese is substituted for the vanadium. The isomerization promotion activity of the catalyst will be substantially equivalent to the unmodified particulate amorphous silicaalumina. The resulting catalyst will also be found to possess excellent carbon monoxide oxidation activity.

Although the invention has been described with particular reference to specific working examples, it is understood that the scope of the invention is not limited thereto but is determined by the breadth of the appended claims.

I claim:

1. In a catalytic process for isomerizing aromatic hydrocarbon compounds containing 8 to 18 carbon atoms in the absence of added free molecular hydrogen wherein the catalyst is periodically regenerated with an oxygen-containing gas stream to remove carbonaceous deposits by converting said deposits to a carbon monoxide-containing gas mixture, the improvement comprising using as the catalyst a mixture consisting of
    (1) about 80 to 99% by weight of a first component consisting of a particulate amorphous silica-alumina composition, and
    (2) about 1 to 20% by weight of a second component consisting of a particulate amorphous silica-alumina composition and 0.05 ppm to 10% by weight of at least one metal or compound of a metal selected from rhenium, ruthenium, osmium, rhodium, iridium, palladium, platinum and mixtures of these.

2. The improved process of claim 1 wherein the amount of metal or metal compound in said second solid particles is about 0.05 ppm to 1000 ppm, calculated as elemental metal based on the total weight of said second solid particles.

3. The improved process of claim 1 wherein said metal or compound of a metal is selected from platinum, palladium, platinum compounds, palladium compounds and mixtures of these and it is present in an amount of about 0.5 to 500 ppm, calculated as elemental metal, based on the total weight of said second solid particles.

4. The improved process of claim 2 wherein said first and second solid particles are present in amounts of about 90 to 99% and about 1 to 10% respectively, based on the total weight of solid particles present.

5. The improved process of claim 2 wherein the mixture of said first and second particles comprises a moving bed.

6. The improved process of claim 1 wherein said aromatic compound is a methyl benzene containing 2 to 5 methyl groups attached to the aromatic nucleus.

7. The improved process of claim 6 wherein said methyl benzene is metaxylene.

8. An improved process of isomerizing metaxylene to orthoxylene and paraxylene comprising, as a first step, contacting, in the absence of added free molecular hydrogen and at a temperature of about 700° F. to 1200° F., metaxylene with a catalyst consisting of about 90 to 99% of a first particulate component which is an amorphous silica-alumina composition and about 1 to 10% of a second particulate component which is an amorphous silica-alumina composition, said second particulate component having impregnated therein about 0.05 ppm to 1% based on the weight of said second particulate component of at least one metal or compound of a metal of the platinum series of the Periodic Table, whereby carbonaceous materials are deposited on said catalyst; and a second step comprising regenerating the catalyst by contacting it with an oxygen-containing gaseous stream at a temperature sufficiently high to burn off at least a portion of the carbonaceous deposits but lower than the catalyst degradation temperature.

9. The process of claim 8 wherein the metal or metal compound is platinum, palladium, mixtures of platinum and palladium, or compounds of these.

* * * * *